United States Patent
Braunling et al.

(10) Patent No.: US 6,490,927 B2
(45) Date of Patent: Dec. 10, 2002

(54) METHOD FOR DETECTING MULTIPLE TYPES OF CORROSION

(75) Inventors: Russell D. Braunling, Eden Prairie, MN (US); Gary S. Whittaker, Kingsport, TN (US); Dane F. Wilson, Oak Ridge, TN (US); George D. Hadden, Saint Paul, MN (US); Sunil Menon, Golden Valley, MN (US)

(73) Assignee: Honeywell International Inc., Morristown, NJ (US)

( * ) Notice: Subject to any disclaimer, the term of this patent is extended or adjusted under 35 U.S.C. 154(b) by 38 days.

(21) Appl. No.: 09/746,095

(22) Filed: Dec. 22, 2000

(65) Prior Publication Data

US 2002/0078752 A1 Jun. 27, 2002

(51) Int. Cl.7 ................................................ G01N 29/10
(52) U.S. Cl. ............................................. 73/597; 73/86
(58) Field of Search ........................ 73/597, 598, 599, 73/600, 86, 627, 629, 630, 602

(56) References Cited

U.S. PATENT DOCUMENTS

| | | | |
|---|---|---|---|
| 3,056,284 A | * 10/1962 | Marsh et al. | ................ 324/700 |
| 4,412,174 A | 10/1983 | Conlon et al. | ................ 324/65 |
| 4,510,793 A | * 4/1985 | Ploegaert et al. | ............. 73/597 |
| 4,539,846 A | * 9/1985 | Grossman | .................... 422/53 |
| 4,872,345 A | * 10/1989 | Dicks | .......................... 73/597 |
| 5,139,627 A | 8/1992 | Eden et al. | ............ 204/153.11 |
| 5,425,867 A | 6/1995 | Dawson et al. | ............. 204/400 |
| 5,526,689 A | 6/1996 | Coulter et al. | ................ 73/592 |
| 5,719,503 A | 2/1998 | Burnett | ....................... 324/534 |
| 6,015,484 A | 1/2000 | Martinchek et al. | ..... 205/775.5 |

FOREIGN PATENT DOCUMENTS

| | | | | |
|---|---|---|---|---|
| GB | 2 238 120 A | * | 5/1991 | .......... G01N/29/04 |
| JP | 61-28841 A | * | 2/1986 | .................... 73/86 |
| JP | 62-266457 A | * | 11/1987 | .................... 73/86 |

* cited by examiner

*Primary Examiner*—Hezron Williams
*Assistant Examiner*—Rose M. Miller
(74) *Attorney, Agent, or Firm*—Kris T. Fredrick

(57) ABSTRACT

A corrosion sensor and method for its use to detect and determine the, type, location, size and growth rate of corrosion of metals and the like in a corrosive environment. The corrosion sensor can distinguish between different types of corrosion such as uniform corrosion, pitting, crevice, and stress corrosion cracking. The sensor detects corrosion conditions of a corrodible metal article in a corrosive environment. It has a metal probe comprised of a metal which is substantially identical to that of the corrodible metal article and a transducer element attached to said probe, which is capable of projecting and receiving ultrasonic or radio frequency signals through the probe. The received signals indicate corrosion of the probe and hence the corrodible metal article.

23 Claims, 3 Drawing Sheets

METHOD FOR DETECTING MULTIPLE TYPES OF CORROSION

BACKGROUND OF THE INVENTION

1. Field of the Invention

The present invention relates to corrosion detection. More specifically, the invention relates to a method for detecting and determining corrosion properties, such as type, location, size, and growth rate in metals and the like in a corrosive environment using a corrosion sensing probe. The invention is also capable of distinguishing between different types of corrosion such as uniform corrosion, and localized corrosion, such as pitting, crevice, and stress corrosion cracking.

2. Description of the Related Art

It has long been known that various forms of corrosion exist which result in the destruction of corrodible materials such as piping, tanks and other metal structures. Two major types of corrosion are uniform and localized corrosion. Uniform corrosion generally includes corrosion of large areas of a corrodible material at a roughly uniform rate. Localized corrosion, such as pitting or cracking, is generally smaller scale corrosion which is harder to detect. Localized corrosion occurs initially in a microscopically small area on a material surface, which eventually becomes larger and deeper, forming pits or cracks in the surface. Localized corrosion, particularly pitting, is hazardous because material is removed in a concentrated area that is not easily recognized. One of the most dangerous consequences of pitting corrosion is a leak in a containment vessel such as a tank or pipeline. The leak typically occurs at a pinhole in a wall of a containment vessel. The majority of the wall will have adequate thickness to contain the vessels contents. However, the resulting leak can be especially dangerous where the contained material is under pressure, at high temperature, or both.

Several methods have been known in the art to detect corrosion of metals. However, these known methods suffer from various disadvantages such as corruption by environmental noise, a requirement of tuning for each application, or an inability to distinguish between different types of corrosion.

One known method involves the analysis and monitoring of electrochemical noise (ECN), or noise generated by the corrosion process. Various statistical analyses may be performed on these noise signals to distinguish corrosion type and corrosion rate in a corroded article. Examples of this ECN approach are described in U.S. Pat. No. 5,139,627, U.S. Pat. No. 5,425,867, and U.S. Pat. No. 6,015,484. There are, however, disadvantages of this ECN method. Electrochemical noise generated by localized corrosion is small and difficult to detect. Environmental noises from motors, circuit breakers, switches, and radio frequency generators in or near the corroded article may mask or obscure the corrosion noise signal, resulting in inaccurate ECN readings.

Another known method involves the use of a radioactive probe to detect pitting corrosion as described in U.S. Pat. No. 4,412,174. According to this method, a radioactive probe is placed into a corrosive stream. As pitting corrosion occurs, pieces of the radioactive probe break off and enter into the stream. The presence of radioactive material is detected by a downstream radiation detector, which allows for the analysis of the probe's corrosion rate. A disadvantage of this approach is that it does not have the capability to differentiate between different types of localized corrosion, such as crevice and pitting.

Acoustic emissions can also be used to detect surface corrosion of an insulated pipe. This method is described in U.S. Pat. No. 5,526,689. This approach involves a transmission of acoustic emissions along the surface of an insulated pipe to locate corroded areas of the pipe. This approach, however, does not include the ability to distinguish between different types of corrosion.

U.S. Pat. No. 5,719,503 involves electromagnetic pulse propagation. According to this method, two electromagnetic sensors are mounted onto a corrodible article. Two pulses are sent from these sensors, and anomalies are examined at the intersection of the two pulses to locate areas of corrosion on the article itself. This approach also does not include the ability to distinguish between different types of corrosion.

It would be desirable to devise a method for corrosion detection which is accurate, reliable, and is able to distinguish among different types of corrosion such as stress corrosion cracking, uniform corrosion, and localized corrosion, such as pitting and cracking.

The present invention provides a solution to this problem. According to the invention, a corrosion sensor is provided which comprises a metal probe attached to a transducer element. The metal probe is inserted into a corrosive environment together with a corrodible article to be tested. The probe and the corrodible article are composed of a substantially identical metal material. A transducer element attached to the probe sends an ultrasonic or radio frequency signal through the probe, and receives any ultrasonic or radio frequency signals which have been reflected by corroded areas of the probe. These reflected signals are analyzed to determine the type, size, location, and growth rate of corrosion conditions in the probe, and thus the corrodible metal article.

SUMMARY OF THE INVENTION

The invention provides a method for detecting corrosion conditions of a corrodible metal article in a corrosive environment which comprises:

a) placing a corrosion sensor into the corrosive environment, which corrosion sensor comprises:
   i) a metal probe comprised of a metal which is substantially identical to that of the corrodible metal article; and
   ii) a transducer element attached to said probe, which transducer element is capable of projecting and receiving ultrasonic or radio frequency signals through the probe;

b) projecting ultrasonic or radio frequency signals from the transducer element through the probe; and c) receiving reflected ultrasonic or radio frequency signals with the transducer element, which reflected ultrasonic or radio frequency signals are reflected by corroded areas of the probe, and generating an electrical response signal to the reflected ultrasonic or radio frequency signals, which indicates a corrosion condition of the probe.

The invention further provides a method for detecting corrosion conditions of a corrodible metal article in a corrosive environment which comprises:

a) placing a corrosion sensor into the corrosive environment, which corrosion sensor comprises:
   i) a metal probe having an elliptical or circular cross section, which probe is comprised of a metal which is substantially identical to that of the corrodible metal article;
   ii) a metal crevice ring:attached around the probe; and iii) a transducer element attached to said probe, which transducer element is capable of projecting and receiving ultrasonic or radio frequency signals through the probe;

b) projecting ultrasonic or radio frequency signals from the transducer element through the probe;

c) receiving reflected ultrasonic or radio frequency signals with the transducer element, which reflected ultrasonic or radio frequency signals are reflected by corroded areas of the probe, and generating an electrical response signal to the reflected ultrasonic or radio frequency signals, which indicates a corrosion condition of the probe;

d) collecting a series of electrical response signals with a computer processor electrically connected to the transducer element; and e) determining a corrosion condition of the probe and the corrodible article from the series of electrical response signals.

The invention still further provides a corrosion sensor for detecting corrosion conditions of a corrodible metal article in a corrosive environment, which corrosion sensor comprises:

a) a metal probe comprised of a metal which is substantially identical to that of the corrodible metal article to be tested; and b) a transducer element attached to said probe, which transducer element is capable of projecting and receiving ultrasonic or radio frequency signals through the probe.

DETAILED DESCRIPTION OF THE PREFERRED EMBODIMENT

Figure 1:
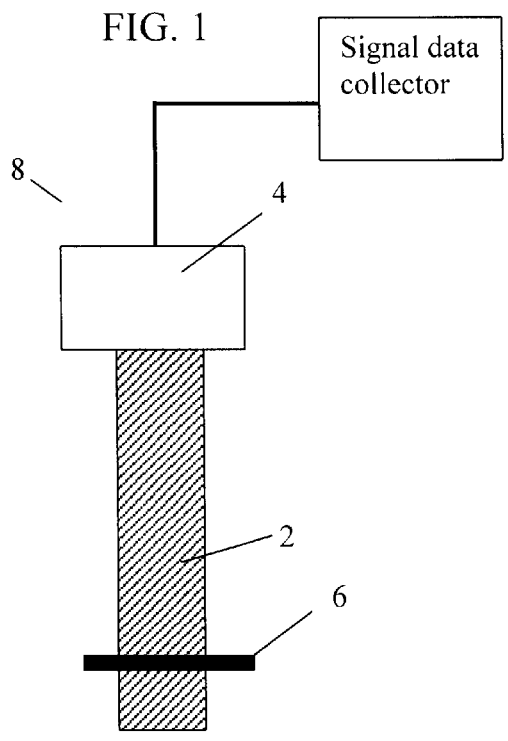
FIG. 1 shows a corrosion sensor of the invention having one external transducer.
Figure 2:
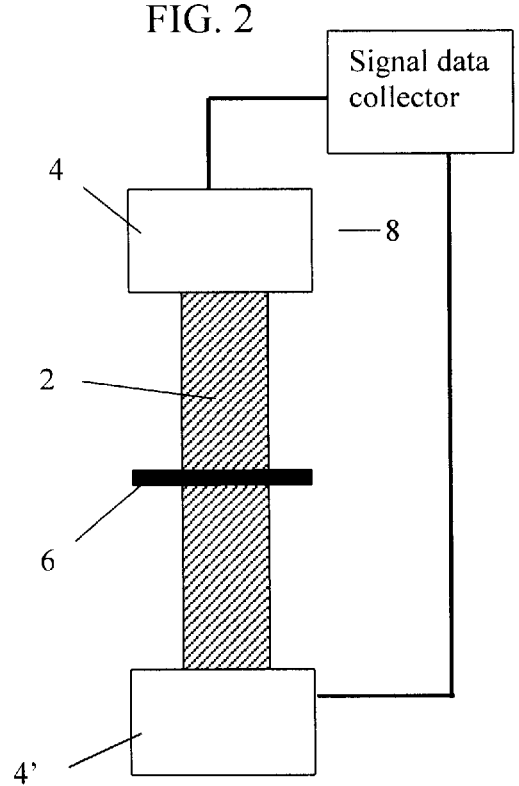
FIG. 2 shows a corrosion sensor of the invention having two external transducers.
Figure 3:
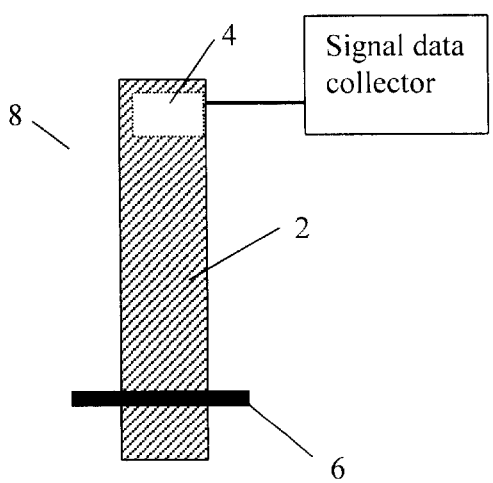
FIG. 3 shows a corrosion sensor of the invention having one internal transducer.
Figure 4:
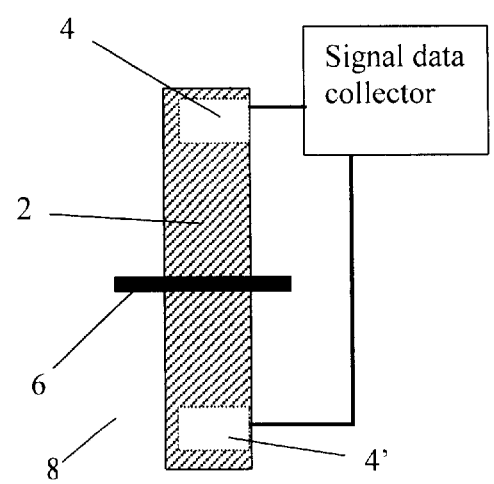
FIG. 4 shows a corrosion sensor of the invention having two internal transducers.
Figure 5:
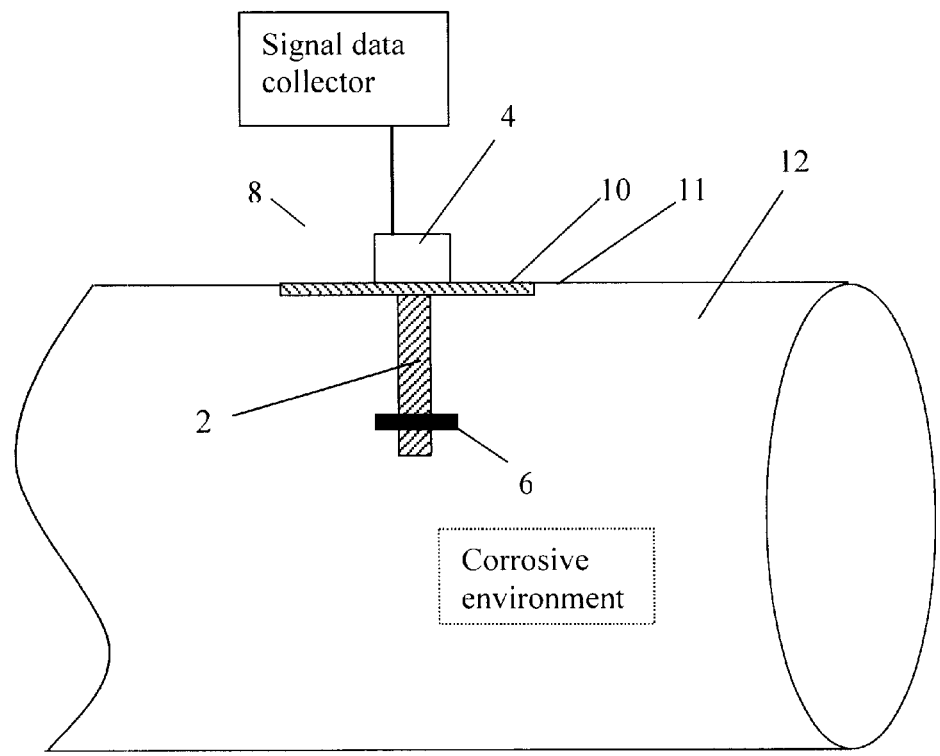
FIG. 5 shows a side view of a corrosion sensor of the invention attached to a pipe containing a corrosive environment.
Figure 6:
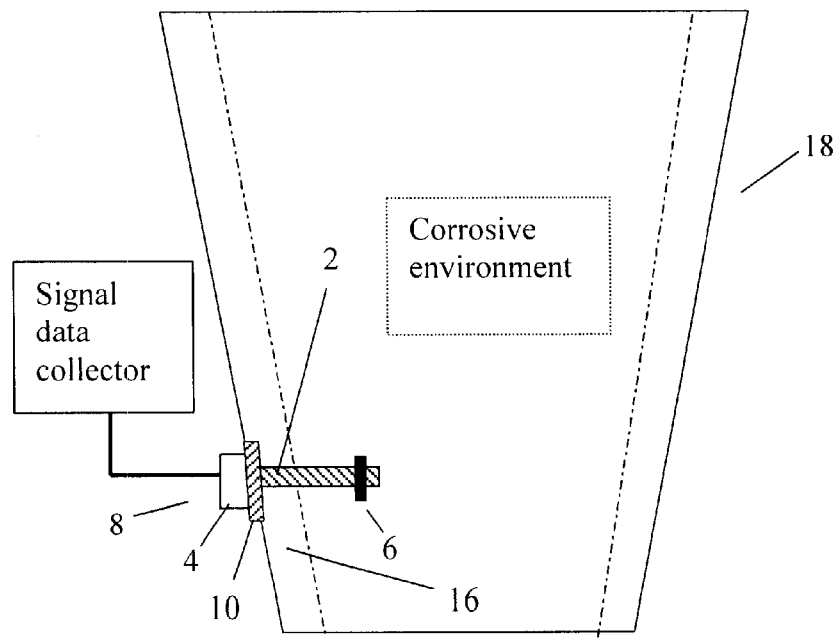
FIG. 6 shows a side view of a corrosion sensor of the invention attached to a wall of a vessel containing a corrosive environment.

The invention provides a method for detecting corrosion conditions of a corrodible metal article in a corrosive environment.

A corrosive environment includes any environment containing a corrosive medium which may cause corrosion of an object or article exposed to that environment. Examples of corrosive media nonexclusively include flowing or nonflowing chemicals including gases such as air, natural gas, process exhaust fumes, and liquids such as acids, bases, organic and inorganic solvents, oils, water, and the like.

A corrodible metal article includes any object or article comprising a metal, which is capable of becoming corroded in a corrosive environment containing a corrosive medium as described above. According to the invention, the term "metal" includes any metal, metal alloy, or combinations of metals and nonmetals. Suitable metals nonexclusively include iron, steels such as stainless steel and super alloy steels, copper, zinc, aluminum, titanium, and alloys and combinations thereof. The corrodible metal article may be in any shape or form. In the practice of the present invention, such articles are typically in the form of metal pipes or vessel walls.

In the practice of the present invention, a corrosion sensor is placed into a corrosive environment. As shown in FIGS. 1–6, a corrosion sensor 8 of the invention is a device which comprises a metal probe 2 attached to a transducer 4. The metal probe 2 may comprise any metal, metal alloy, or combinations thereof such as those described above for the corrodible metal article. It is important that the material of the metal probe 2 is substantially identical to that of the corrodible metal article to be tested. In a preferred embodiment, the metal probe 2 comprises stainless steel, most preferably stainless steel 304. The metal probe 2 may be in any shape or form, and may be solid or hollow. Preferably, the metal probe 2; is of a shape having a circular or elliptical cross section. In a most preferred embodiment, the metal probe 2 is of a shape having an elliptical cross-section. This shape serves to induce stress points on the metal probe 2 for the formation and detection of stress corrosion cracking, which is described below.

The probe may optionally include one or more stress inducing features which serve to induce stress on the probe, thus providing fixed locations for corrosion formation and detection. Examples of stress inducing features may include stress inducing shapes, and stress inducing attachments. A stress inducing shape is a particular shape or configuration of the metal probe which may induce stress on probe itself for the formation and detection of corrosion, particularly stress cracking corrosion. For example, in one embodiment the probe includes a bent portion which may induce stress on the probe. In another embodiment, stress may be induced on a probe which is of a shape having an elliptical cross section. A stress inducing attachment includes objects which may be attached onto or around the probe, which may induce stress on the probe for the formation and detection of corrosion. Stress inducing attachments preferably comprise substantially the same material as that of the probe.

The probe may also comprise a metal crevice ring 6, preferably of the same material as the probe which is attached around the probe to provide fixed locations for the formation and detection of crevice corrosion, as described below.

According to the invention, a transducer element is attached to the metal probe 2. The transducer element preferably comprises at least one transducer 4, 4' as shown in FIGS. 1–6. Suitable transducers nonexclusively include piezoelectric transducers, electromagnetic acoustic transducers (EMAT), magnetorestrictive transducers, interdigital ultrasonic transducers, and active transducers such as millimeter wave transducers. Piezoelectric transducers are preferred, the most preferred being angled piezoelectric transducers. Suitable piezoelectric transducers are commercially available from Tektrend International of Montreal, Canada. Suitable methods of attaching the transducer elements to the probe nonexclusively include gluing, welding, soldering, and the like. The transducer element may be attached to the metal probe 2 internally or externally, and may be done in any arrangement and by any suitable means known in the art which would allow the transducer element to be capable of projecting and receiving ultrasonic or radio frequency signals through the metal probe 2. In one embodiment of the invention, shown in FIG. 1, the transducer element comprises one transducer 4 which is externally attached to a first end of the metal probe 2. In another embodiment, shown in FIG. 2, the transducer element comprises two transducers, 4 and 4', wherein one is externally attached to a first end of the metal probe 2 and the other is externally attached to a second end of the metal probe 2. In another embodiment, shown in FIG. 3, the transducer element comprises one transducer 4 which is internally attached to the metal probe 2. In still another embodiment, shown in FIG. 4, the transducer element comprises two transducers, 4 and 4', wherein both are internally attached to the metal probe.

In use, the corrosion sensor is placed into a corrosive environment. This is typically done by attaching the sensor to the corrodible metal article in the corrosive environment. This may be done in any suitable manner which would expose the metal probe to the. corrosive environment, such as by inserting the probe through the corrosive metal article and into the corrosive environment, or by flush mounting the sensor to the corrosive metal article. In one embodiment, shown in FIG. 5, a sensor 8 is attached via a seal 10, through a wall 11 of a corrodible metal pipe 12, wherein the transducer 4 is on the outside of the pipe 12, and the metal probe 2 is exposed to a corrosive environment inside the pipe 12. In another embodiment, shown in FIG. 6, a sensor 8 is attached to a corrodible metal vessel 18 wherein the probe 2 is attached via a seal 10 within a wall 16 of the vessel 18, which vessel 18 contains a corrosive environment. Various other embodiments can be implemented in the scope of the present invention.

At various periods of time,.ultrasonic or radio frequency signals, such as ultrasonic waves, radio waves, millimeter waves, and the like, are projected from the transducer element, through the metal probe. The voltage, frequency, incident angles, length, and other parameters of these signals may vary depending on the size of the probe and the type of transducer used, and may be determined by those skilled in the art. For example, the operating frequency of an ultrasonic transducer should be chosen to have a wavelength that is comparable in size to the size of the corrosion defect that it detects. Therefore, corrosion defects such as pitting that have size in the millimeter or sub millimeter range require an operating frequency in the MHz range. As an example, an ultrasonic transducer may generate an ultrasonic pulse through a probe, said pulse having a frequency ranging from about 1 MHz to about 10 MHz, more preferably from about 1.5 MHz to about 8 MHz, and most preferably from about 2 MHz to about 5 MHz. Radio frequency transducers may generate pulses having frequencies ranging from about 1 gigahertz to about 5 gigahertz. Radio frequency transducers are available from Prolyx, L.L.C. of San Jose, Calif.

If any corrosion areas exist in the metal probe, the ultrasonic or radio frequency signals sent through the probe to those areas by the transducer element will be reflected by the corrosion, and sent back to the transducer element. These reflected ultrasonic or radio frequency signals, if any, are received by the transducer element, which then generates an electrical response signal to the reflected ultrasonic or radio frequency signals, indicating a corrosion condition of the metal probe. Corrosion conditions include any properties of corroded areas, such as corrosion size, location, growth rate, and type. Types of corrosion nonexclusively include stress corrosion cracking, uniform corrosion, and localized corrosion such as pitting corrosion and crevice corrosion. Stress corrosion cracking (SCC) is the formation of fine cracks due to the combined influence of tensile stress and a corrosive medium. Uniform corrosion is generally characterized as an even thinning of a corrodible article over a large surface area. Pitting corrosion is a localized form of corrosion by which small cavities or holes are produced in the corrodible article. Crevice corrosion is a localized form of corrosion typically formed in crevices such as under washers, gaskets, clamps, and the like.

A series of such electrical response signals may be collected by a signal data collector which may be electrically connected to the transducer element. In a preferred embodiment of the invention, the signal data collector includes an ultrasonic testbed including, a broadband receiver which receives the ultrasonic electrical response signals sent from the transducer. These signals are then sent to a digitizer which changes the response signals from analog to digital, and displays the signals on an oscilloscope or graphic processing information display. Typically, the graphically displayed signals are a function of echo receive time and amplitude which are indicative of the distance along the probe and the amount of corrosion at that distance. These data are useful in determining various characteristics of the corrosion. A preferred signal data collector comprises a computer microprocessor for system operation and control, and for using corrosion algorithms for calculating type, location, size, and growth rate of corrosion. This determination of corrosion conditions can be analyzed to survey the structural integrity of corrodible metal articles which are subjected to corrosive environments. The parameters of importance depend on the environment conditions, and are easily determinable by those skilled in the art.

The following non-limiting examples serve to illustrate the invention. It will be appreciated that variations in proportions and alternatives in elements of the components of the invention will be apparent to those skilled in the art and are within the scope of the present invention.

EXAMPLE 1

A corrosion detector is assembled by externally bonding a piezoelectric transducer to one end of a metal probe. The probe is composed of a stainless steel rod having an elliptical cross section.

Figure 7:
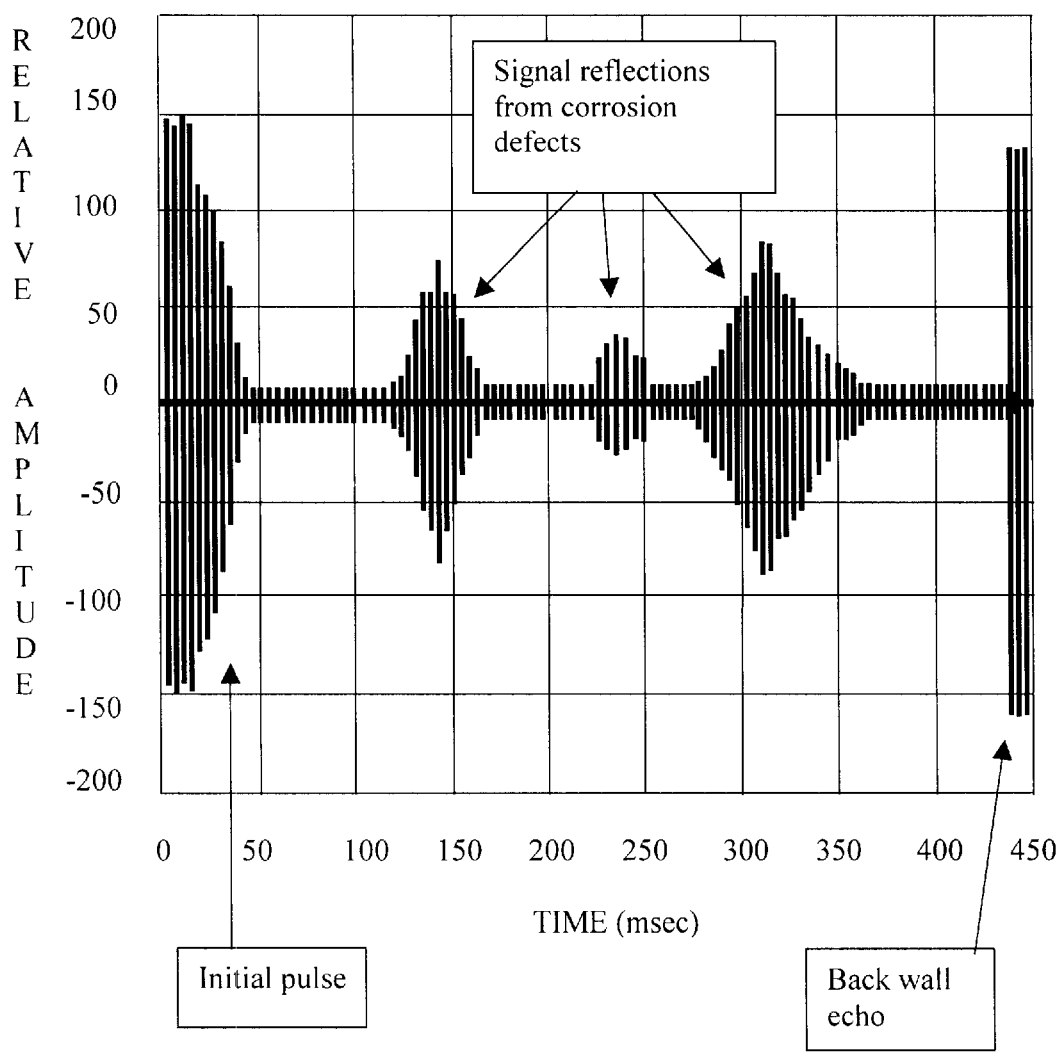
FIG. 7 shows a graphical representation of a reflected ultrasonic pulse projected through a probe having corrosion defects.

Holes are drilled into the probe to simulate corrosion of the probe. These holes have diameters of 3.2 mm, 1.6 mm and 3.2 mm respectively, and have a depth of 0.9 mm. Ultrasonic waves are projected from the transducer through the probe. It is noticed that some of the ultrasonic waves are reflected from the drilled holes. These reflected waves are received and collected by the transducer. The received ultrasonic waves then induce a voltage in the transducer, which is analyzed by a signal data collector which is electrically attached to the transducer. The time for receiving the echo and the intensity of the reflected sound are graphically illustrated in FIG. 7. This graph shows an initial ultrasonic pulse which is reflected from the simulated corrosion at the drilled hole points as well as the back wall of the probe.

EXAMPLE 2

A corrosion detector is assembled by externally bonding a piezoelectric transducer to the end of a metal probe. The probe is composed of a stainless steel rod having an elliptical cross section. The corrosion detector is securely placed through an opening in a sidewall of a stainless steel pipe such that the transducer remains outside of the pipe. Natural gas is allowed to flow through the pipe such that the metal probe is in contact with the natural gas.

Ultrasonic waves are projected from the transducer through the probe. Reflected waves are received and collected by the transducer. The received ultrasonic waves then induce a voltage from the transducer, which is analyzed by a signal data collector which is electrically attached to the transducer. These analyzed signals are used to establish a baseline. Ultrasonic waves are then projected and received in the same manner through the probe once an hour for 30 days. Reflected ultrasonic signals are collected and analyzed, and compared to the baseline in order to estimate the degree of corrosion of the probe, and hence on the inside wall of the pipe.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A method for detecting corrosion conditions of a corrodible metal article in a corrosive environment which comprises:
   a) placing a corrosion sensor into the corrosive environment, which corrosion sensor comprises:
      i) a metal probe comprised of a metal which is substantially identical to that of the corrodible metal article; and
      ii) a transducer element attached to said probe, which transducer element is capable of projecting and receiving ultrasonic or radio frequency signals through the probe;
   b) projecting ultrasonic or radio frequency signals from the transducer element through the probe; and
   c) receiving reflected ultrasonic or radio frequency signals with the transducer element, which reflected ultrasonic or radio frequency signals are reflected by corroded areas of the probe, and generating an electrical response signal to the reflected ultrasonic or radio frequency signals, which indicates a corrosion condition of the probe.

2. The method of claim 1 wherein the projected and reflected signals are ultrasonic signals.

3. The method of claim 1 wherein the projected and reflected signals are radio frequency signals.

4. The method of claim 1, which further comprises collecting a series of electrical response signals with a signal data collector electrically connected to the transducer element.

5. The method of claim 4, which further comprises determining a corrosion condition of the probe and the corrodible article from the series of electrical response signals.

6. The method of claim 1 wherein the metal probe further comprises at least one stress inducing feature.

7. The method of claim 6 wherein the metal probe further comprises a metal crevice ring attached around the probe.

8. The method of claim 4 wherein the signal data collector comprises a computer microprocessor.

9. The method of claim 5 wherein the corrosion condition determined comprises the size of corrosion of the probe and the corrodible article are determined.

10. The method of claim 5 wherein the corrosion condition determined comprises the location of corrosion of the probe and the corrodible article are determined.

11. The method of claim 5 wherein the corrosion condition determined comprises the growth rate of corrosion of the probe and the corrodible article are determined.

12. The method of claim 5 wherein the corrosion condition determined comprises the type of corrosion of the probe and the corrodible article are determined.

13. The method of claim 12 wherein the amount of pitting corrosion of the probe and the corrodible article are determined.

14. The method of claim 12 wherein amount of uniform corrosion of the probe and the corrodible article are determined.

15. The method of claim 12 wherein an amount of crevice corrosion of the probe and the corrodible article are determined.

16. The method of claim 12 wherein the amount of stress corrosion cracking of the probe and the corrodible article are determined.

17. A method for detecting corrosion conditions of a corrodible metal article in a corrosive environment which comprises:
   a) placing a corrosion sensor into the corrosive environment, which corrosion sensor comprises:
      i) a metal probe having an elliptical or circular cross section, which probe is comprised of a metal which is substantially identical to that of the corrodible metal .article;
      ii) a metal crevice ring attached around the probe; and
      iii) a transducer element attached to said probe, which transducer element is capable of projecting and receiving ultrasonic or radio frequency signals through the probe;
   b) projecting ultrasonic or radio frequency signals from the transducer element through the probe;
   c) receiving reflected ultrasonic or radio frequency signals with the transducer element, which reflected ultrasonic or radio frequency signals are reflected by corroded areas of the probe, and generating an electrical response signal to the reflected ultrasonic or radio frequency signals, which indicates a corrosion condition of the probe;
   d) collecting a series of electrical response signals with a computer processor electrically connected to the transducer element; and
   e) determining a corrosion condition of the probe and the corrodible article from the series of electrical response signals.

18. A corrosion sensor for detecting corrosion conditions of a corrodible metal article in a corrosive environment, which corrosion sensor comprises:
   a) a metal probe comprised of a metal which is substantially identical to that of the corrodible metal article: to be tested; and
   b) a transducer element attached to said probe, which transducer element is capable of projecting and receiving ultrasonic or radio frequency signals through the probe.

19. The corrosion sensor of claim 18 wherein the probe has an elliptical cross section.

20. The corrosion sensor of claim 18 wherein the probe has a circular cross section.

21. The corrosion sensor of claim 18 wherein the metal probe further comprises at least one stress inducing feature.

22. The corrosion sensor of claim 21 wherein the metal probe further comprises a metal crevice ring attached around the probe.

23. The corrosion sensor of claim 18 further comprising a signal data collector.

* * * * *